(12) United States Patent
Holland et al.

(10) Patent No.: US 9,248,196 B2
(45) Date of Patent: Feb. 2, 2016

(54) REBAMIPIDE COMPLEXES AND COCRYSTALS

(75) Inventors: Joanne Holland, Cambridge (GB); Daniel Gooding, Cambridge (GB); Alan Chorlton, Newmarket (GB)

(73) Assignee: NUFORMIX LIMITED (GB)

( * ) Notice: Subject to any disclaimer, the term of this patent is extended or adjusted under 35 U.S.C. 154(b) by 0 days.

(21) Appl. No.: 14/001,007

(22) PCT Filed: Feb. 24, 2012

(86) PCT No.: PCT/IB2012/050871
§ 371 (c)(1),
(2), (4) Date: Oct. 25, 2013

(87) PCT Pub. No.: WO2012/114317
PCT Pub. Date: Aug. 30, 2012

(65) Prior Publication Data
US 2014/0039005 A1 Feb. 6, 2014

Related U.S. Application Data

(60) Provisional application No. 61/446,573, filed on Feb. 25, 2011.

(51) Int. Cl.
*A61K 31/4704* (2006.01)
*C07D 215/227* (2006.01)
*A61K 47/48* (2006.01)

(52) U.S. Cl.
CPC ....... *A61K 47/48061* (2013.01); *A61K 31/4704* (2013.01); *A61K 47/4803* (2013.01); *A61K 47/48038* (2013.01); *C07D 215/227* (2013.01)

(58) Field of Classification Search
CPC .............. A61K 31/4704; C07D 215/227
USPC .......................................... 514/312; 546/157
See application file for complete search history.

(56) References Cited

U.S. PATENT DOCUMENTS

| 4,578,381 | A | * | 3/1986 | Uchida et al. ............... 514/235.2 |
| 5,637,597 | A | | 6/1997 | Matsuda et al. |
| 6,060,486 | A | | 5/2000 | Urashima et al. |

FOREIGN PATENT DOCUMENTS

| JP | 2839847 B2 | 12/1998 |
| JP | 3093661 B2 | 10/2000 |

(Continued)

OTHER PUBLICATIONS

Kojima; International Journal of Pharmaceutics, 2010, 399, 52-59.*
(Continued)

*Primary Examiner* — Janet L Andres
*Assistant Examiner* — Daniel Carcanague
(74) *Attorney, Agent, or Firm* — J.A. Lindeman & Co., PLLC

(57) ABSTRACT

New rebamipide complexes and new rebamipide cocrystals are disclosed, specifically a 1:1 rebamipide nicotinamide complex, a 1:1 rebamipide nicotinamide cocrystal, a 1:1 rebamipide 2,4-dihydroxybenzolc acid complex, and a 1:1 rebamipide 2,4-dihydroxybenzoic acid cocrystal. Pharmaceutical compositions containing a rebamipide complex or cocrystal of the invention and a pharmaceutically acceptable carrier and methods of treatment are also disclosed.

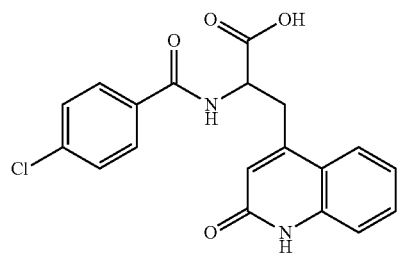

6 Claims, 11 Drawing Sheets

(56) References Cited

FOREIGN PATENT DOCUMENTS

| KR | 10-2004-0104020 | A  | 12/2004 |
| WO | 97/09045        | A1 | 3/1997  |
| WO | 2005/011811     | A1 | 2/2005  |
| WO | 2005/070892     | A1 | 8/2005  |

OTHER PUBLICATIONS

Kashima; Clinical Ophthalmology, 2014, 8, 1003-1010.*

International Search Report for PCT International Application No. PCT/IB2012/050871, mailed Jun. 29, 2012.
Written Opinion of the International Searching Authority for PCT International Application No. PCT/IB2012/050871, mailed Aug. 25, 2013.
Remington's Pharmaceutical Sciences, 18th Ed., Table of Contents (Mack Publishing Company, Easton, Pa., 1990).
English-language abstract of JP 2839847.
English-language abstract of JP 3093661.
English-language abstract of KR 10 2004-0104020.

* cited by examiner

REBAMIPIDE COMPLEXES AND COCRYSTALS

CROSS-REFERENCE TO RELATED APPLICATIONS

Priority is claimed to U.S. Application Ser. No. 61/446,573, filed 25 Feb. 2011, the disclosure of which incorporated herein by reference.

FIELD OF THE INVENTION

The invention relates to new rebamipide complexes and new rebamipide cocrystals. In particular, the invention relates to a 1:1 rebamipide nicotinamide complex and a 1:1 rebamipide nicotinamide cocrystal. The invention also relates to a 1:1 rebamipide 2,4-dihydroxybenzoic acid complex and a 1:1 rebamipide 2,4-dihydroxybenzoic acid cocrystal. The invention also relates to pharmaceutical compositions containing a rebamipide complex or cocrystal of the invention as well as methods of treatment using them.

BACKGROUND

Rebamipide, 2-(4-chlorobenzamido)-3-(2-oxo-1,2-dihydroquinolin-4-yl)propanoic acid, shown below, is an agent that exhibits anti-inflammatory and antiulcer effects on the gastrointestinal tract.

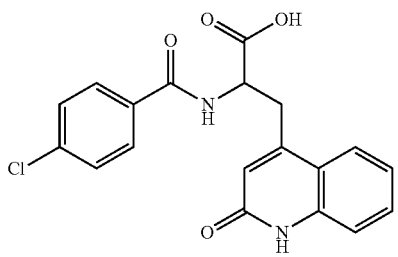 [SMILES: O=C(NC(Cc1cc(=O)[nH]c2ccccc12)C(=O)O)c1ccc(Cl)cc1]

Rebamipide occurs as a white crystalline powder that is odourless and has a bitter taste. It is very slightly soluble in methanol and ethanol but is practically insoluble in water. Rebamipide is identified by CAS Registry Number: 90098-04-7. A method of preparation of rebamipide is described in JP-B-63-35623.

Rebamipide is known as an agent for improving both subjective and objective symptoms of diseases such as gastric ulcer, duodenal ulcer, gastritis and other like diseases. It has also been disclosed that rebamipide is useful in the treatment of various other diseases, for example, for the treatment a ulcerative colitis (cf., Kazuya Makiyama, "Study of the treatment of ulcerative colitis by enema therapy of rebamipide"), for stomatitis (Japanese Patent No. 2839847), for accelerating salivation (WO/2005/011811) and for inhibiting carcinogenesis of the digestive tract (WO/1997/009045). Rebamipide is also known for having an increasing action of goblet cell density in the eye, an increasing action of mucus in the eye and an increasing action of lacrimal fluid, and it is already known as an agent for treating dry eye (JP-A-9-301866), Rebamipide is marketed by Otsuka Pharmaceutical Co., Ltd under the Mucosta® tradename. It is currently indicated for the treatment of gastric mucosal legions (erosions, bleeding, redness and edema) in acute gastritis and acute exacerbation of chronic gastritis. The typical dosage in adults is one 100 mg tablet three times daily.

There is a need therefore to develop new forms of rebamipide that have improved dissolution, solubility and/or increased bioavailability. The rebamipide complexes and cocrystals of this invention answer such needs.

Although therapeutic efficacy is the primary concern for an active pharmaceutical ingredient (API), the salt and solid state form (i.e., the crystalline or amorphous form) of a drug candidate can be critical to its pharmacological properties, such as bioavailability, and to its development as a viable API. Recently, crystalline forms of API's have been used to alter the physicochemical properties of a particular API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid state properties of the crystalline form of the API, they can significantly impact the selection of a compound as an API, the ultimate pharmaceutical dosage form, the optimization of manufacturing processes, and absorption in the body. Moreover, finding the most adequate solid state form for further drug development can reduce the time and the cost of that development.

Obtaining crystalline forms of an API is extremely useful in drug development but is not necessarily predictable. It permits better characterization of the drug candidate's chemical and physical properties. It is also possible to achieve desired properties of a particular API by forming a cocrystal of the API and a coformer. Crystalline forms often have better chemical and physical properties than the free base in its amorphous state. Such crystalline forms may, as with the cocrystal of the invention, possess more favorable pharmaceutical and pharmacological properties or be easier to process than known forms of the API itself. For example, a cocrystal, if achieved, may have different dissolution and solubility properties than the API itself and can be used to deliver APIs therapeutically. New drug formulations comprising a cocrystal of a given API may have superior properties over its existing drug formulations. They may also have better storage stability.

Another potentially important solid state property of an API is its dissolution rate in aqueous fluid. The rate of dissolution of an active ingredient in a patient's stomach fluid may have therapeutic consequences since it impacts the rate at which an orally administered active ingredient may reach the patient's bloodstream.

A cocrystal of any API is a new and distinct chemical composition of the API and the coformer(s) and generally possesses distinct crystallographic and spectroscopic properties when compared to those of the API and coformer(s) individually. Crystallographic and spectroscopic properties of crystalline forms are typically measured by X-ray powder diffraction (XRPD) and single crystal X-ray crystallography, among other techniques. Cocrystals often also exhibit distinct thermal behavior. Thermal behavior is measured in the laboratory by such techniques as capillary melting point, thermogravimetric analysis (TGA) and differential scanning calorimetry (DSC).

SUMMARY OF THE INVENTION

The invention relates to new rebamipide complexes and new rebamipide cocrystals. In particular, the invention relates to a 1:1 rebamipide nicotinamide complex, a 1:1 rebamipide nicotinamide cocrystal, a 1:1 rebamipide 2,4-dihydroxybenzoic acid complex, and a 1:1 rebamipide 2,4-dihydroxybenzoic acid cocrystal. The invention relates to pharmaceutical compositions containing a rebamipide complex or cocrystal of the invention and a pharmaceutically acceptable carrier. The rebamipide complexes and cocrystals may be used in the same way as rebamipide treat or prevent disorders relating to gastric ulcer, duodenal ulcer, gastritis, ulcerative colitis, and stomatitis. The rebamipide complexes and cocrystals may also be used in the same way as rebamipide to accelerate salivation, to inhibit carcinogenesis of the digestive tract, to increase action of goblet cell density in the eye, to increase the action of mucus in the eye, to increase the action of lacrimal fluid, as well as to treat dry eye.

DETAILED DESCRIPTION

Figure 1:
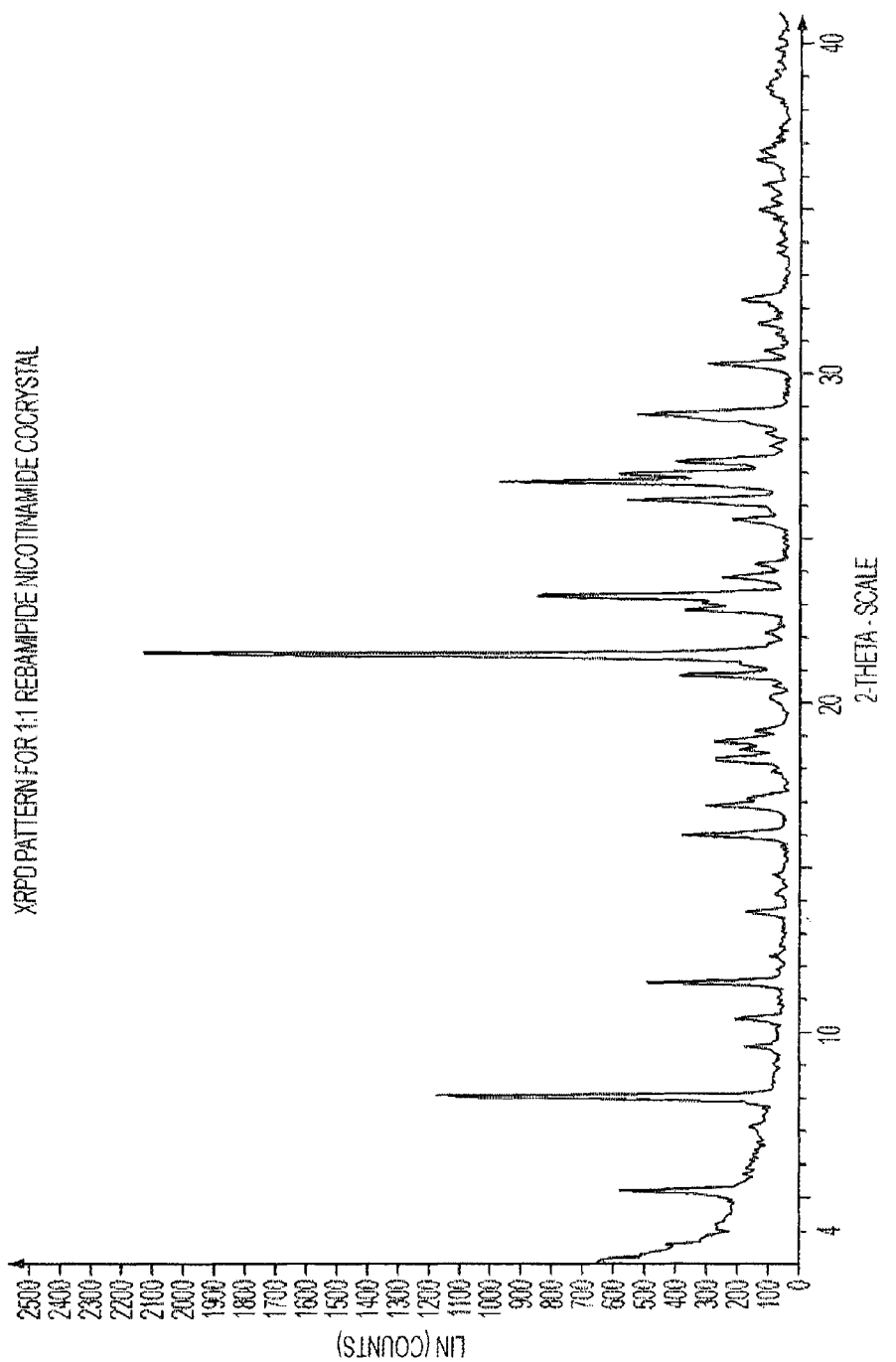
FIG. 1 shows an XRPD pattern for the 1:1 rebamipide nicotinamide cocrystal.

The invention relates to improvements of the physiochemical and/or the pharmaceutical properties of rebamipide. Disclosed herein are new rebamipide complexes and new rebamipide cocrystals. In particular, the invention relates to a 1:1 rebamipide nicotinamide complex, a 1:1 rebamipide nicotinamide cocrystal, a 1:1 rebamipide 2,4-dihydroxybenzoic acid complex, and a 1:1 rebamipide 2,4-dihydroxybenzoic acid cocrystal. The therapeutic uses of the rebamipide complexes and cocrystals of the invention are described below as well as therapeutic compositions containing them. The cocrystals and the methods used to characterize them are described below.

Therapeutic Uses of Rebamipide Complexes and Cocrystals

The invention further relates to the therapeutic use of the rebamipide complexes and cocrystals of the invention, a 1:1 rebamipide nicotinamide complex, a 1:1 rebamipide nicotinamide cocrystal, a 1:1 rebamipide 2,4-dihydroxybenzoic: acid complex, and a 1:1 rebamipide, 2,4-dihydroxybenzoic acid cocrystal, to treat or prevent disorders relating to gastric ulcer, duodenal ulcer gastritis, ulcerative colitis, and stomatitis. The rebamipide complexes and cocrystals may also he used in the same way as rebamipide to accelerate salivation, to inhibit carcinogenesis of the digestive tract, to increase action of goblet cell density in the eye, to increase the action of mucus in the eye, to increase the action of lacrimal fluid, as well as to treat dry eye. Accordingly, the invention relates to method of treating such a disorder comprising the step of administering to a patient in need thereof a therapeutically effective amount of a rebamipide complex or cocrystal of the invention or of administering to a patient in need thereof a therapeutic composition containing a rebamipide complex or cocrystal of the invention.

The term "treatment" or "treating" means any treatment of a condition or disorder in a mammal, including: preventing or protecting against the condition or disorder, that is, causing the clinical symptoms not to develop; inhibiting the condition or disorder, that is, arresting or suppressing the development of clinical symptoms; and/or relieving the condition or disorder (including the relief of discomfort associated with the condition or disorder), that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" the condition or disorder. The term "protection" is meant to include "prophylaxis."

Pharmaceutical Compositions Containing the Rebamipide Complexes and Cocrystals

The invention also relates to pharmaceutical compositions comprising a therapeutically effective amount of a rebamipide complex or cocrystal according to the invention and a pharmaceutically acceptable carrier (also known as a pharmaceutically acceptable excipient). As mentioned above, these pharmaceutical compositions are therapeutically useful to treat or prevent disorders such as those discussed above.

A pharmaceutical composition of the invention may be in any pharmaceutical form which contains a rebamipide complex or cocrystal according to the invention. The pharmaceutical composition may be, for example, a tablet, capsule, liquid suspension, injectable, topical, or transdermal. Liquid pharmaceutical compositions may be prepared comprising a rebamipide complex of the invention. The pharmaceutical compositions generally contain, for example, about 1% to about 99% by weight of a rebamipide complex or cocrystal of the invention and, for example, 99% to 1% by weight of at least one suitable pharmaceutical excipient. In one embodiment, the composition may be between about 5% and about 75% by weight of a rebamipide complex or cocrystal of the invention with the rest being at least one suitable pharmaceutical excipient or at least one other adjuvant, as discussed below.

A "therapeutically effective amount of a rebamipide complex or cocrystal according to the invention" is that which correlates to about 50- about 150 mg of rebamipide itself. As discussed above, rebamipide is marketed by Otsuka Pharmaceutical Co., Ltd under the Mucosta® tradename. It is currently prescribed for the treatment of gastric mucosal legions (erosions, bleeding, redness and edema) in acute gastritis and acute exacerbation of chronic gastritis. The typical dosage in adults is one 100 mg tablet three times daily.

The actual amount required for treatment of any particular condition or disorder or any particular patient may depend upon a variety of factors including, for example, the disease state being treated and its severity; the specific pharmaceutical composition employed; the age, body weight, general health, sex and diet of the patient; the mode of administration; the time of administration; the route of administration; and the rate of excretion of rebamipide; the duration of the treatment; any drugs used in combination or coincidental with the specific compound employed; and other such factors well known in the medical arts. These factors are discussed in Goodman and Gilman's "The Pharmacological Basis of Therapeutics", Tenth Edition, A. Gilman, J. Hardman and L. Limbird, eds., McGraw-Hill Press, 155-173, 2001, which is incorporated herein by reference.

Depending on the type of pharmaceutical composition, the pharmaceutically acceptable carrier may be chosen from any one or a combination of carriers known in the art. The choice of pharmaceutically acceptable carrier depends upon the pharmaceutical form arid the desired method of administration to be used. For a pharmaceutical composition of the invention, that is one having a rebamipide cocrystal of the invention, a carrier should be chosen that maintains the crystalline form. In other words, the carrier should not substantially after the rebamipide cocrystal. Nor should the carrier be otherwise incompatible with the rebamipide cocrystal used, such as by producing any undesirable biological effect or otherwise interacting in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, a rebamipide complex or cocrystal of the invention may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, aliginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric add, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Liquid dosage forms may be aqueous, may contain a pharmaceutically acceptable solvent as well as traditional liquid dosage form excipients known in the art which include, but are not limited to, buffering agents, flavorants, sweetening agents, preservatives, and stabilizing agents.

Compositions for rectal administrations are, for example, suppositories that may be prepared by mixing a rebamipide complex or cocrystal of the invention with, for example, suitable non-irritating excipients or carriers such as cocoa butter, polyethyleneglycol or a suppository wax, which may be solid at ordinary temperatures but may be liquid at body temperature and, therefore, melt while in a suitable body cavity and release the active component therein.

Because the crystalline form of a rebamipide cocrystal may be maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). A rebamipide complex and cocrystal according to the invention may also be used as to formulate liquid or injectable pharmaceutical compositions. Administration of a rebamipide compound or cocrystal in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, intrasystemically, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the musculoskeletal condition to be treated.

EXAMPLES

The following analytical method were used to characterize the rebamipide cocrystals of the invention:

X-ray powder diffraction: X-ray powder diffraction patterns for the samples were acquired on a Bruker D8 diffractometer using CuKα radiation (40 kV, 40 mA), θ-2θgoniometer, V4 receiving slits, a Ge monochromator and a Lynxeye detector. The instrument is performance checked using a certified Corundum standard (NIST 1976). The data were collected over an angular range of 2° to 42° 2Θ using a step size of 0.05° 2Θ and a step time of 0.5 seconds. Samples run under ambient conditions were prepared as flat plate specimens using powder as received without grinding. Approximately, 35 mg of the sample was gently packed into a cavity cut into polished, zero background (510) silicon wafer. All samples were analysed using Diffrac Plus EVA v11.0.0.2 or v13.0.0.2.

Thermal analysis—Differential Scanning Calorimetry (DSC): DSC data was collected on a TA instruments Q2000 equipped with a 50 position autosampler. The calibration for thermal capacity was carried out using sapphire and the calibration for the energy and temperature was carried out using certified indium. Typically 0.8-1.2 mg of each sample, in a pin-holed aluminium pan, was heated at 10° C./min from 25° C. to 350° C. A purge of dry nitrogen at 50 ml/min was maintained over the sample. The instrument control software was Advantage for Q series v2.8.0.392 and Thermal Advantage v4.8.3. All data analysis was performed using Universal Analysis v4.3A software.

Solution Proton NMR: $^1$H-NMR spectra were recorded on a Bruker 400 MHz spectrometer equipped with an auto-sampler and controlled by a DRX400 console. The samples were dissolved in d6-DMSO for analysis. The data was acquired using ICON-NMR v4.0.4 (build 1) running with Topspin v1.3 (patch level 8) using the standard Bruker loaded experiments.

$^{13}$C Solid State NMR: The spectra were obtained using a Varian VNMRS spectrometer operating at 100.56 MHz and a 4 mm (rotor o.d.) magic-angle spinning probe. They were recorded using cross polarisation with acquisition conditions appropriate to the sample. The spectral referencing was with respect to neat, external tetramethylsilane (by setting the high-frequency line from adamantine to 38.5 ppm).

Example 1.

1:1 Rebamipide Nicotinamide Cocrystal 1.1 Preparation of a 1:1 Rebamipide Nicotinamide Cocrystal Rebamipide (100 mg) was weighed into a glass vial. 15 ml of a saturated solution of nicotinamide in nitromethane was added and the vial sealed. The resulting slurry was placed in a shaker and matured for 5 days (RT to 50° C. on an 8 hour cycle, heating to 50° C. for 4 hours and then cooling to RT for a further 4 hours). The product was then filtered under vacuum and dried in a vacuum oven at 50° C. overnight.

1.2 XRPD Characterisation of a 1:1 Rebamipide Nicotinamide Cocrystal

The experimental XRPD pattern of the 1:1 rebamipide nicotinamide cocrystal is shown in FIG. 1. Table 1 lists the angles °2θ+0.2°2θ, and d-spacing of the peaks identified in the experimental XRPD pattern of FIG. 1. The entire list of peaks, or a subset thereof, may be sufficient to characterize the cocrystal. For example, the cocrystal may be characterised by at least three peaks or at least five peaks selected from the peaks at 5.2, 9.5, 10.4, 11.5, 13.6, 16.0, 20.9 and 21.5°2θ+0.2°2θ as well as by an XRPD pattern substantially similar to FIG. 1.

TABLE 1

| Angle °2θ ± 0.2 °2θ | d value Angstrom | Intensity % |
| --- | --- | --- |
| 2.3 | 39.24 | 84.5 |
| 2.6 | 33.96 | 58.9 |
| 5.2 | 17.14 | 26.9 |
| 7.1 | 12.42 | 7.5 |
| 8.0 | 11.01 | 54.9 |
| 9.5 | 9.29 | 8.1 |
| 10.4 | 8.50 | 9.6 |

TABLE 1-continued

| Angle °2θ ± 0.2 °2θ | d value Angstrom | Intensity % |
| --- | --- | --- |
| 11.5 | 7.68 | 22.9 |
| 12.3 | 7.20 | 4.4 |
| 13.6 | 6.50 | 8.1 |
| 14.2 | 6.23 | 3.6 |
| 14.7 | 6.00 | 3.9 |
| 16.0 | 5.54 | 17.6 |
| 16.9 | 5.24 | 14.2 |
| 17.1 | 5.17 | 8.0 |
| 18.3 | 4.85 | 12.7 |
| 18.6 | 4.76 | 9.1 |
| 18.8 | 4.71 | 12.9 |
| 19.1 | 4.63 | 6.6 |
| 20.2 | 4.40 | 4.5 |
| 20.9 | 4.26 | 18.0 |
| 21.5 | 4.13 | 100.0 |
| 22.1 | 4.02 | 5.2 |
| 22.9 | 3.88 | 17.5 |
| 23.3 | 3.82 | 39.7 |
| 23.8 | 3.74 | 11.6 |
| 24.2 | 3.67 | 6.6 |
| 25.5 | 3.48 | 10.1 |
| 26.1 | 3.41 | 26.1 |
| 26.7 | 3.33 | 45.4 |
| 26.9 | 3.31 | 27.5 |
| 27.4 | 3.26 | 18.8 |
| 27.8 | 3.21 | 4.5 |
| 28.2 | 3.16 | 5.2 |
| 28.8 | 3.10 | 24.6 |
| 30.3 | 2.95 | 13.8 |
| 30.7 | 2.91 | 5.5 |
| 31.3 | 2.86 | 3.7 |
| 31.5 | 2.83 | 6.3 |
| 32.3 | 2.77 | 8.8 |
| 34.7 | 2.58 | 4.2 |
| 35.0 | 2.56 | 6.3 |
| 35.4 | 2.54 | 4.3 |
| 35.8 | 2.51 | 5.6 |
| 36.5 | 2.46 | 6.5 |
| 36.8 | 2.44 | 6.1 |
| 38.8 | 2.32 | 4.8 |
| 41.9 | 2.16 | 5.4 |

1.3 DSC of 1:1 Rebamipide Nicotinamide Cocrystal

Figure 2:
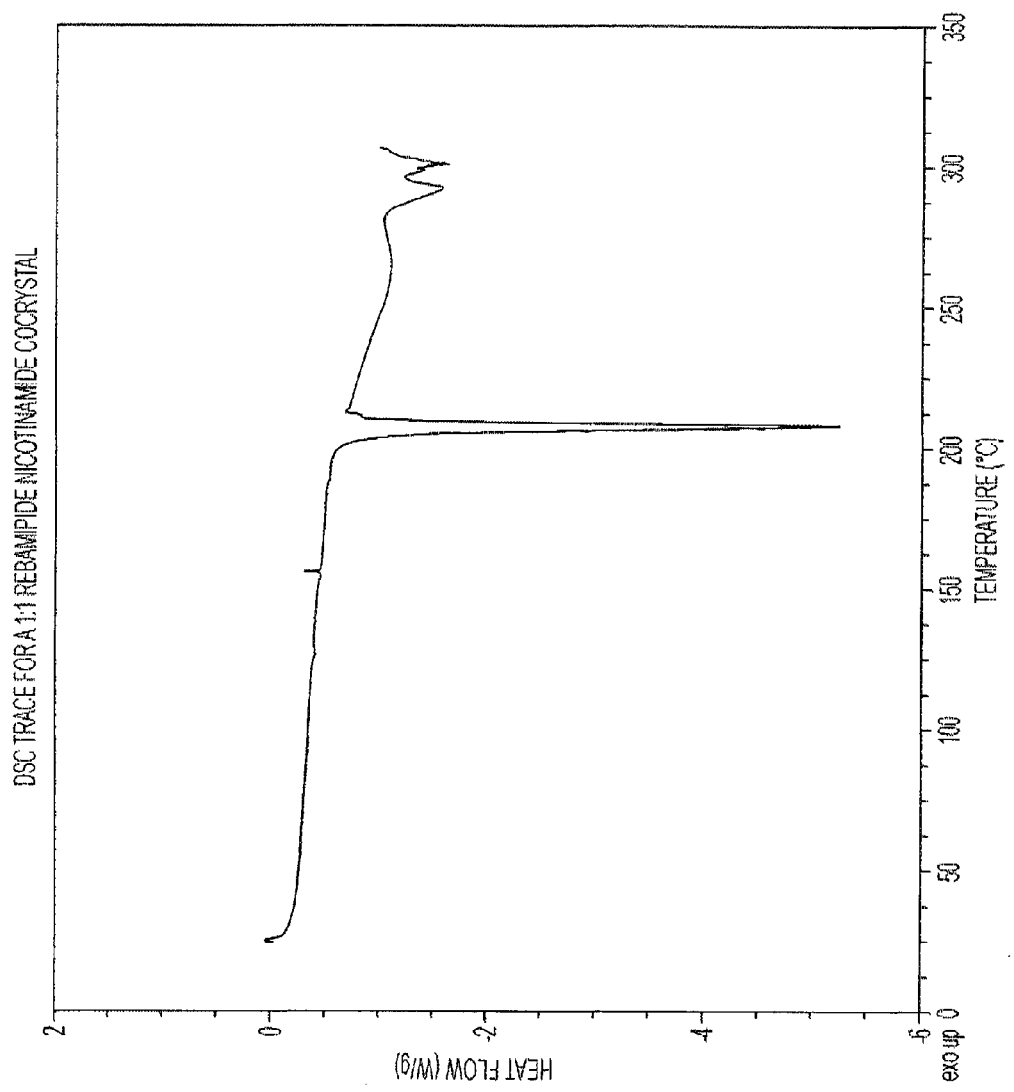
FIG. 2 shows a DSC trace for the 1:1 rebamipide nicotinamide cocrystal.

The differential scanning calorimetry (DSC) trace, FIG. 2, shows an endotherm with an onset temperature of 205.6° C. and a peak maximum of 208.1° C.

1.4 $^1$H NMR Spectrum of a 1:1 Rebamipide Nicotinamide Cocrystal

Figure 3:
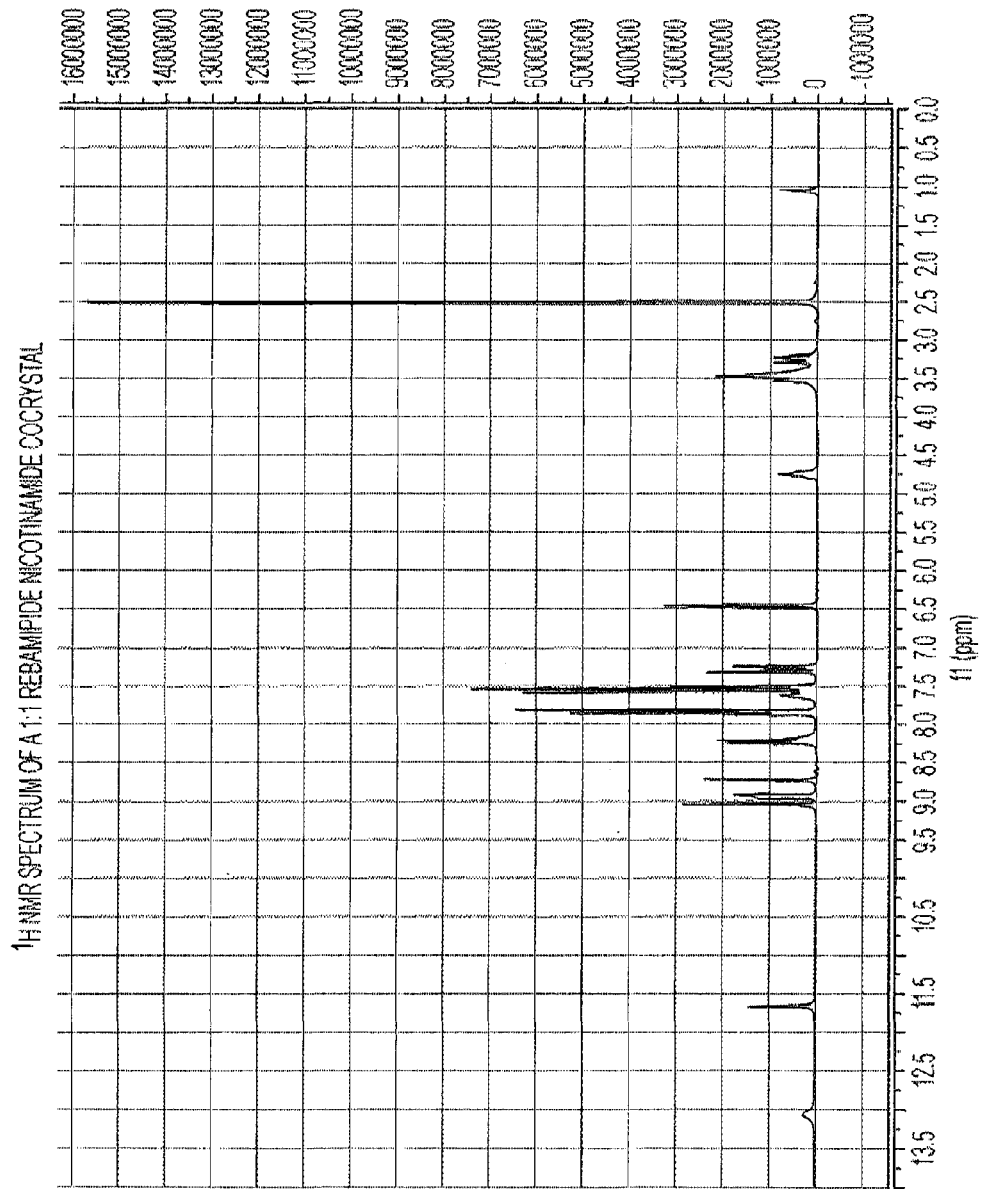
FIG. 3 shows the $^1$H NMR spectrum of the 1:1 rebamipide nicotinamide cocrystal.

The $^1$H NMR spectrum of the 1:1 rebamipide nicotinamide cocrystal, shown in FIG. 3, displays the following peaks: $^1$H NMR (400 MHz, d6-DMSO) δ: 13.07 (1H), 11.66 (1H), 9.04 (1H), 8.93 (1H), 8.71 (1H), 8.22 (1H), 8.17 (1H), 7.83 (3H), 7.62 (1H), 7.54 (4H), 7.27 (2H), 6.45 (1H), 4.75 (1H), 3.48 (1H) and 3.24 (1H). The peak at 6.45 ppm corresponds to one CH proton of rebamipide. Comparison of the integration of this peak with that at 8.71 ppm, which corresponds to one proton on the aromatic ring of nicotinamide, indicates that the cocrystal has an API:coformer stoichiometry of 1:1.

Figure 4:
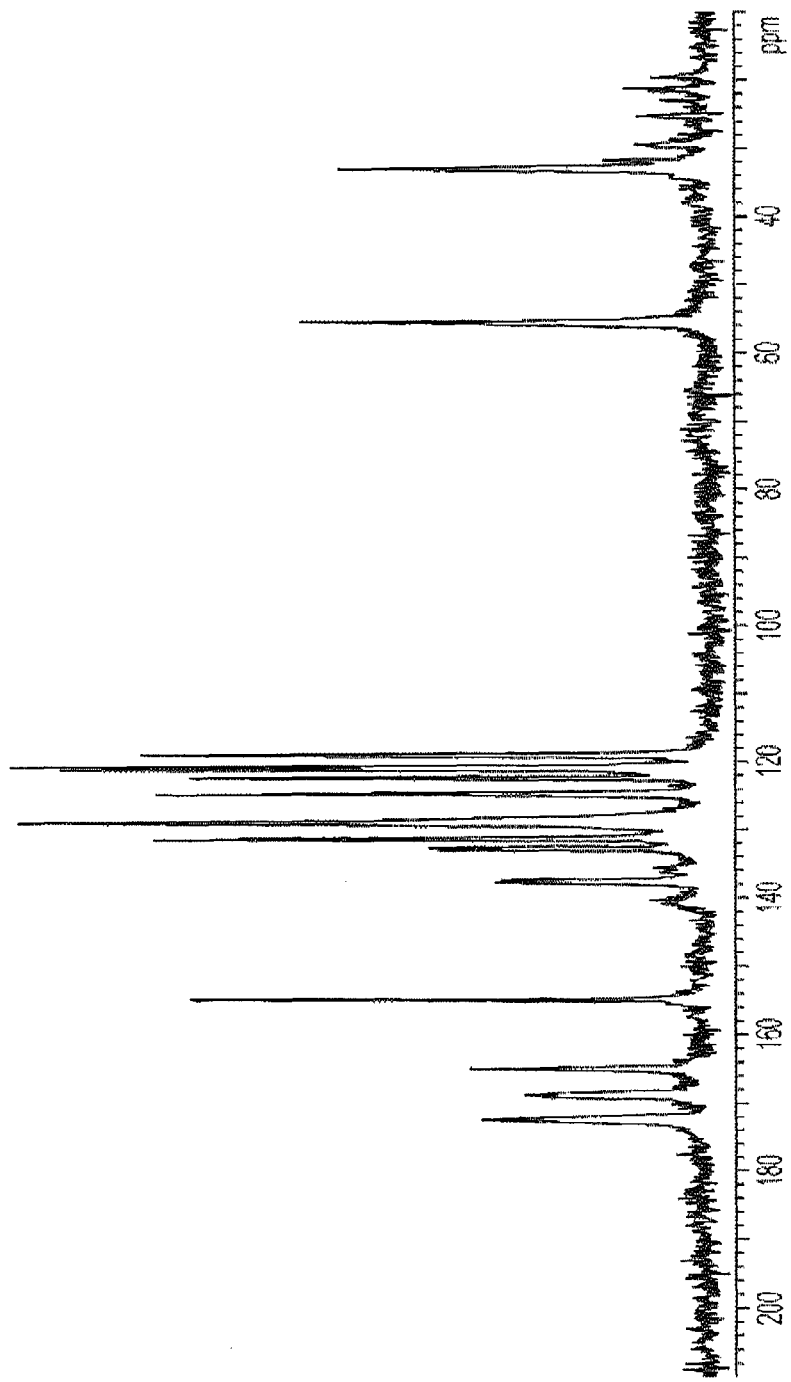
FIG. 4 shows the $^{13}$C solid state NMR spectrum of rebamipide.
Figure 5:
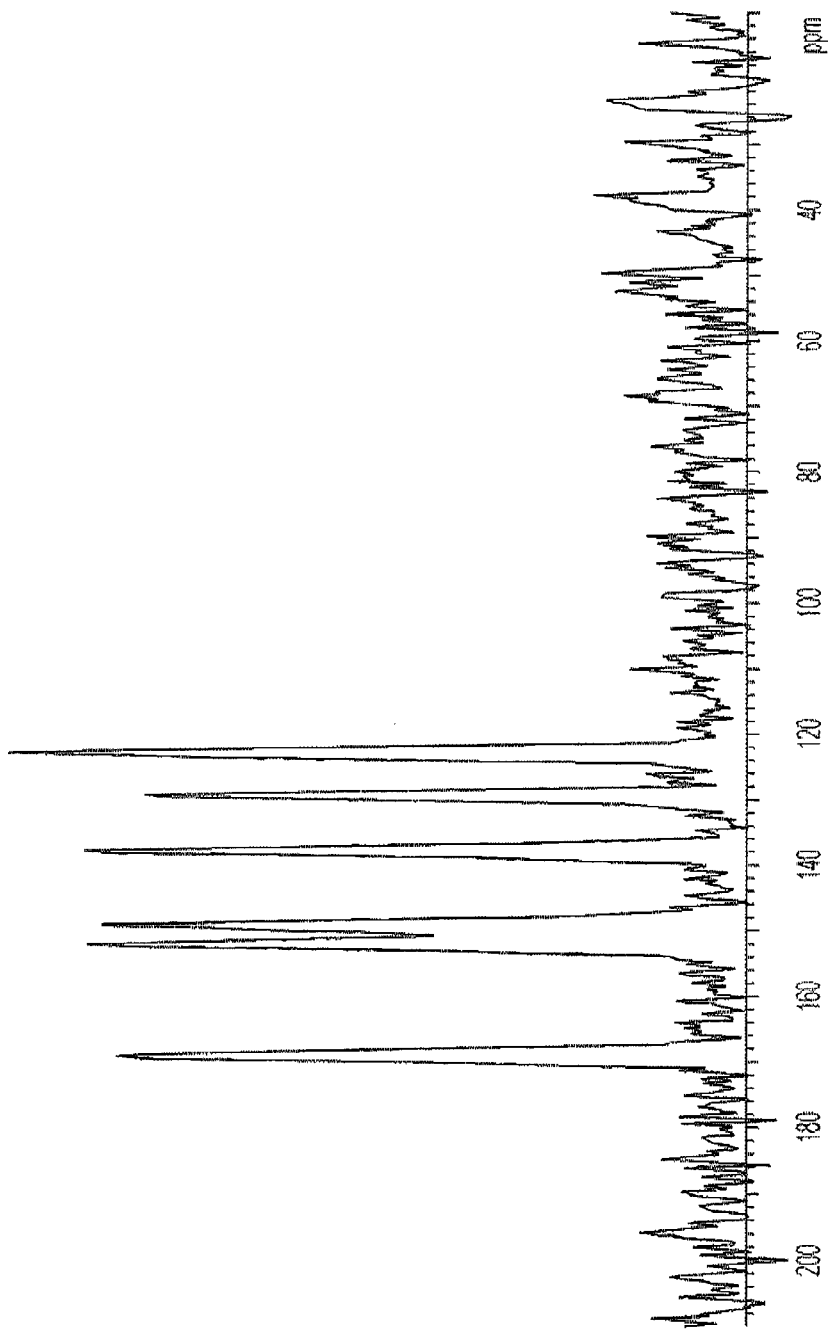
FIG. 5 shows the $^{13}$C solid state NMR spectrum of nicotinamide.

1.5 $^{13}$C Solid State NMR Analysis of the 1:1 Rebamipide Nicotinamide Cocrystal The $^{13}$C solid state NMR spectrum of rebamipide is shown in FIG. 4. A series of test measurements was carried out that showed that the pure rebamipide sample relaxed in such a way that a 10 s recycle delay was appropriate for this compound. When it was attempted to obtain the $^{13}$C spectra of a pure sample nicotinamide under these same acquisition conditions it was found that the nicotinamide gave no signal. It was necessary to increase the recycle delay time to 600 s in order to obtain the spectrum of nicotinamide (FIG. 5).

Figure 6:
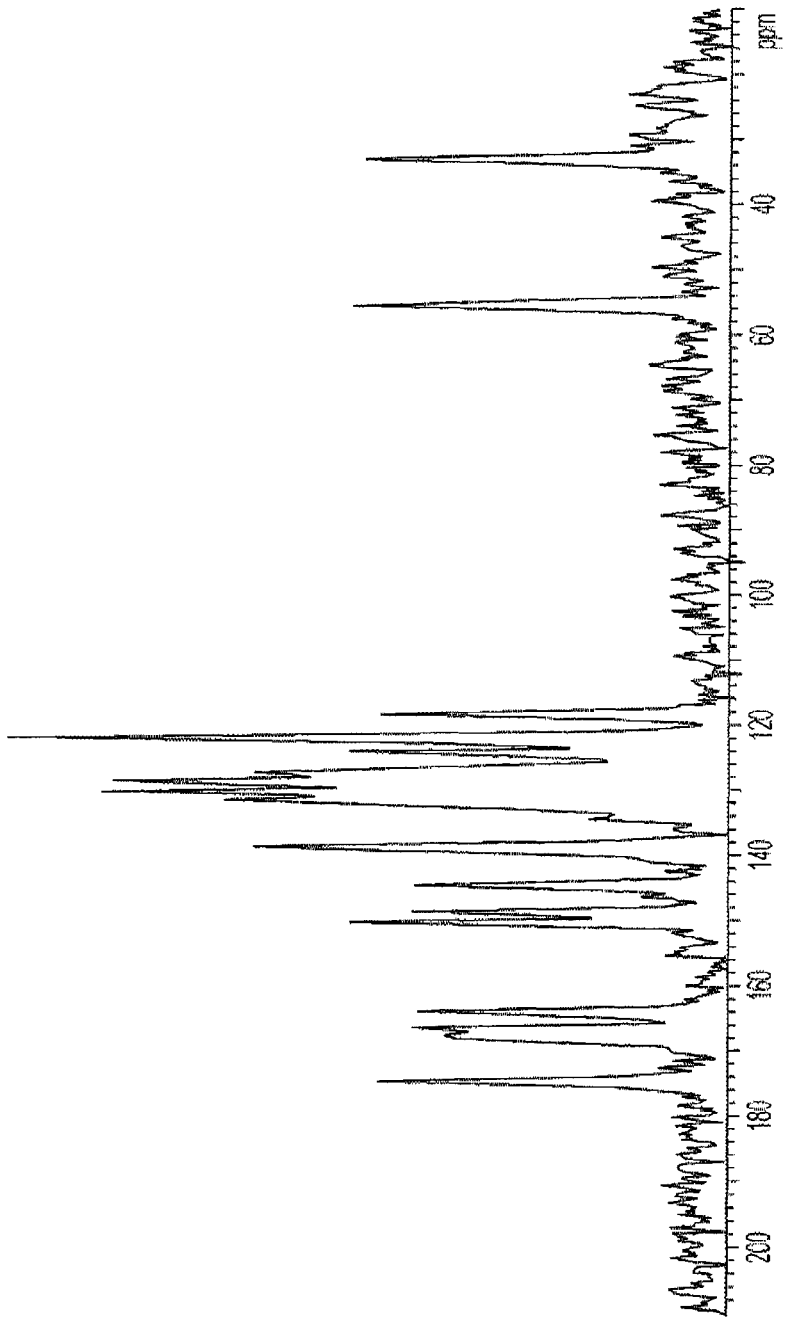
FIG. 6 shows the $^{13}$C solid state NMR spectrum of the 1:1 rebamipide nicotinamide cocrystal.

The $^{13}$C spectrum obtained for the 1:1 rebamipide nicotinamide cocrystal is shown in FIG. 6. Table 2 lists the characteristic shifts, ppm +/−0.5 ppm, observed in the experimental $^{13}$C NMR spectrum of FIG. 6. It can be seen that the 1:1 rebamipide nicotinamide cocrystal spectrum is significantly different to those of the pure rebamipide or nicotinamide. A recycle delay of 60 s was found to be necessary to obtain the spectrum of the cocrystal. A series of test measurements showed that this delay was appropriate for all the lines in the spectrum. The fact that there is a common, sample wide ($^{1}$H T$_1$) relaxation behaviour suggests that the two components are strongly interacting and are present in the same crystal.

TABLE 2

| Chemical Shift (ppm ± 0.5 ppm) |
|---|
| 174.7 |
| 166.6 |
| 164.1 |
| 150.4 |
| 148.7 |
| 144.7 |
| 138.9 |
| 131.8 |
| 130.4 |
| 128.9 |
| 124.3 |
| 122.3 |
| 118.4 |
| 55.6 |
| 33.2 |

Example 2

1:1 Rebamipide 2,4-Dihydroxybenzoic Acid Cocrystal 2.1 Preparation of a 1:1 Rebamipide 2,4-Dihydroxybenzoic Add Cocrystal Rebamipide (200 mg) and 2,4-dihydroxybenzoic acid (83 mg) were weighed into a glass vial. Nitromethane (2.0 ml) was added and the vial sealed. The resulting slurry was placed in a shaker and matured for 5 days (RT to 50° C. on an 8 hour cycle, heating to 50° C. for 4 hours and then cooling to RT for a further 4 hours). The product was then filtered under vacuum and dried in a vacuum oven at 50° C. overnight.

Figure 7:
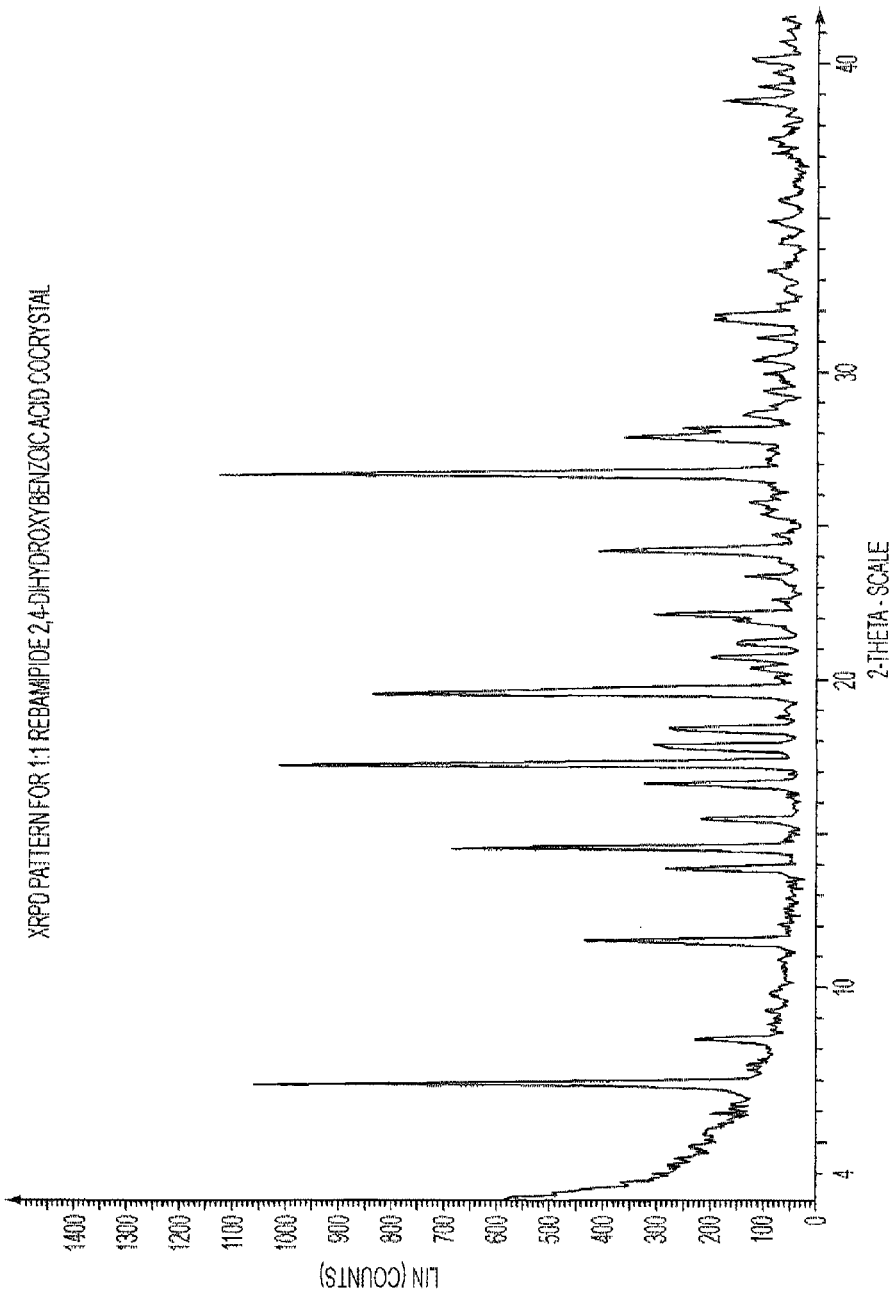
FIG. 7 shows an XRPO pattern for the 1:1 rebamipide 2,4-dihydroxybenzoic acid cocrystal.

2.2 XRPD Characterisation of a 1:1 Rebamipide 2,4-Dihydroxybenzoic Acid Cocrystal The experimental XRPD pattern of the 1:1 rebamipide 2,4-dihydroxybenzoic acid cocrystal is shown in FIG. 7. Table 3 lists the angles °2θ+0.2°2θ, and d-spacing of the peaks identified in the experimental XRPD pattern of FIG. 7. The entire list of peaks, or a subset thereof, may be sufficient to characterize the cocrystal. For example, the cocrystal may be characterised by a t least three peaks or by at least five peaks selected from the peaks at 6.9, 11.5, 13.9, 14.5, 15.4, 16.6, 17.3 and 18.4°2θ±0.2°2θ as well as by an XRPD pattern substantially similar to FIG. 7.

TABLE 3

| Angle °2θ ± 0.2 °2θ | d value Angstrom | Intensity % |
|---|---|---|
| 5.3 | 16.61 | 18.9 |
| 6.9 | 12.83 | 94.0 |
| 8.3 | 10.66 | 20.2 |
| 9.2 | 9.66 | 7.9 |
| 9.8 | 9.03 | 7.4 |
| 11.5 | 7.69 | 35.7 |
| 13.9 | 6.39 | 23.3 |

TABLE 3-continued

| Angle °2θ ± 0.2 °2θ | d value Angstrom | Intensity % |
|---|---|---|
| 14.5 | 6.09 | 60.8 |
| 15.4 | 5.74 | 17.8 |
| 16.6 | 5.34 | 26.6 |
| 17.3 | 5.13 | 89.6 |
| 17.8 | 4.98 | 25.2 |
| 18.4 | 4.83 | 22.9 |
| 18.8 | 4.72 | 6.5 |
| 19.6 | 4.54 | 74.0 |
| 20.3 | 4.36 | 10.2 |
| 20.7 | 4.29 | 16.3 |
| 21.2 | 4.19 | 12.5 |
| 21.8 | 4.07 | 13.0 |
| 22.1 | 4.02 | 24.9 |
| 22.6 | 3.93 | 7.1 |
| 23.4 | 3.81 | 11.1 |
| 24.2 | 3.68 | 33.7 |
| 24.7 | 3.60 | 7.2 |
| 25.3 | 3.51 | 8.7 |
| 25.7 | 3.46 | 10.5 |
| 26.3 | 3.39 | 7.8 |
| 26.7 | 3.34 | 100.0 |
| 27.8 | 3.20 | 29.4 |
| 28.1 | 3.17 | 20.7 |
| 28.6 | 3.12 | 11.5 |
| 28.9 | 3.08 | 7.4 |
| 29.4 | 3.04 | 8.5 |
| 29.9 | 2.98 | 8.2 |
| 30.4 | 2.94 | 9.7 |
| 31.1 | 2.87 | 9.2 |
| 31.7 | 2.82 | 16.6 |
| 32.2 | 2.77 | 6.4 |
| 32.7 | 2.74 | 5.5 |
| 33.3 | 2.69 | 7.9 |
| 34.3 | 2.61 | 5.7 |
| 34.9 | 2.57 | 7.7 |
| 35.6 | 2.52 | 6.2 |
| 37.2 | 2.42 | 7.0 |
| 37.6 | 2.39 | 7.9 |
| 38.8 | 2.32 | 14.5 |
| 39.3 | 2.29 | 9.4 |
| 39.7 | 2.27 | 7.0 |
| 40.1 | 2.25 | 10.2 |
| 40.7 | 2.21 | 6.2 |

2.3 DSC of 1:1 Rebamipide 2,4-Dihydroxybenzoic Acid Cocrystal

Figure 8:
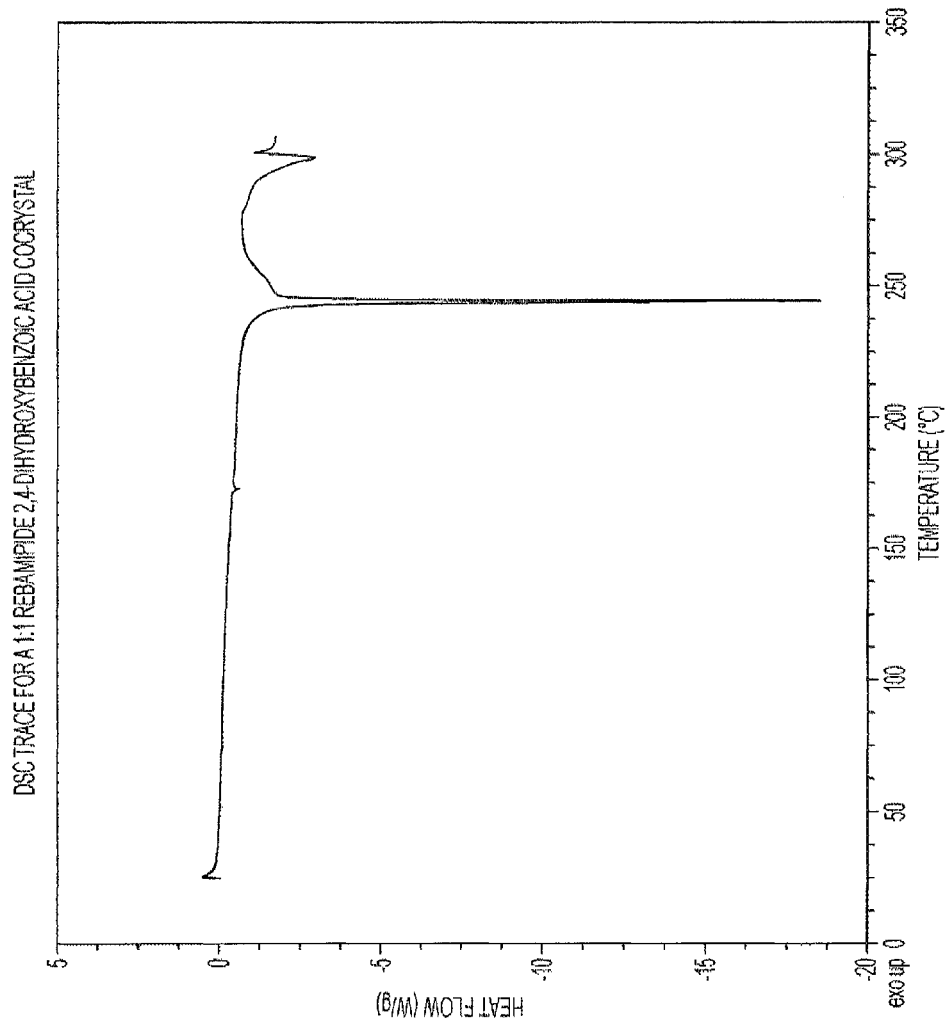
FIG. 8 shows a DSC trace for the 1:1 rebamipide 2,4-dihydroxybenzoic acid cocrystals

The differential scanning calorimetry (DSC) trace, FIG. 8, shows an endotherm with an onset temperature of 243.7 and a peak maximum of 244.2° C.

Figure 9:
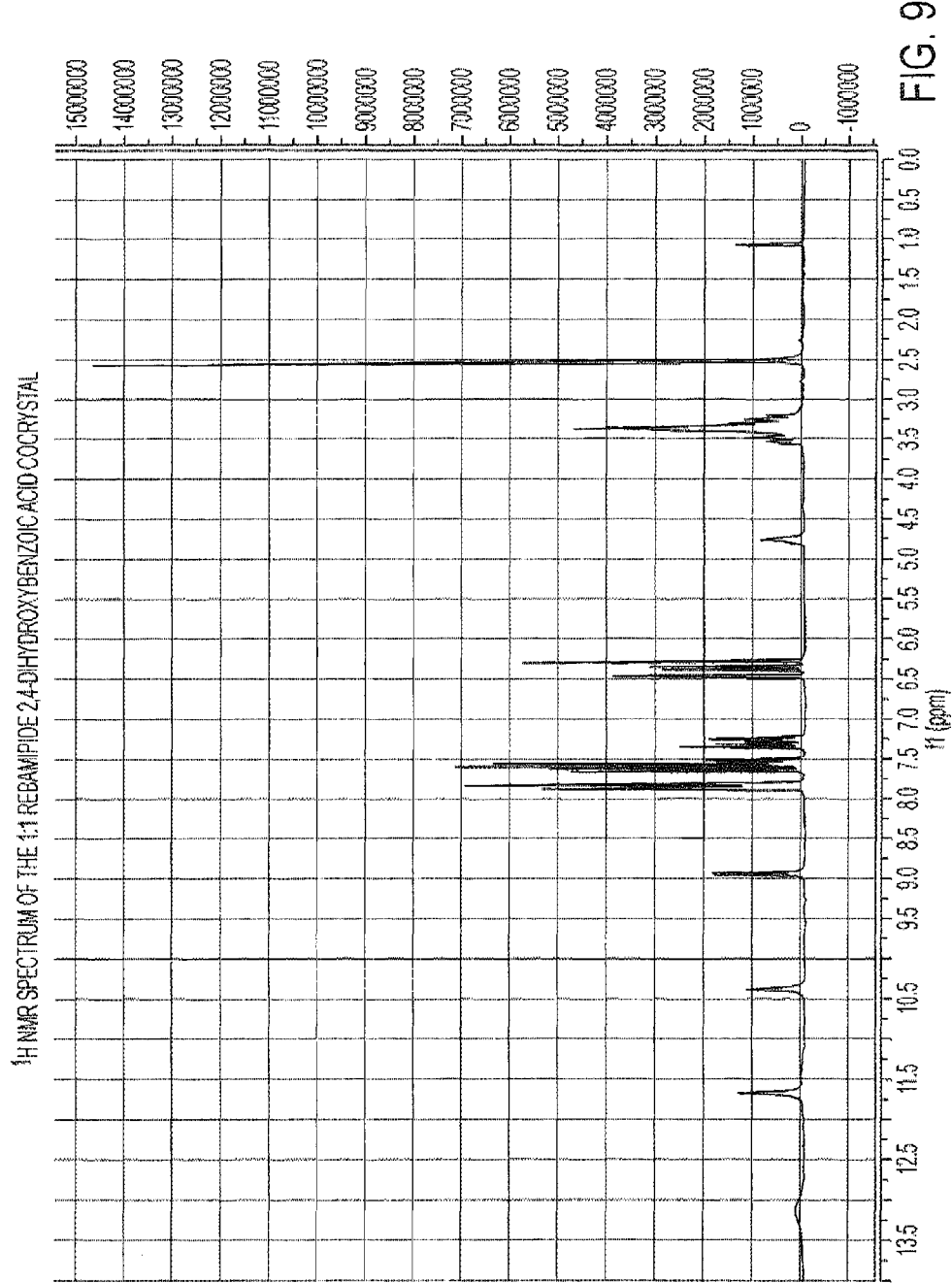
FIG. 9 shows the $^1$H NMR spectrum of the 1:1 rebamipide 2,4-dihydroxybenzoic acid cocrystal.

2.4 $^{1}$H NMR Spectrum of a 1:1 Rebamipide 2,4-Dihydroxybenzoic Acid Cocrystal The $^{1}$H NMR spectrum of the 1:1 rebamipide 2,4-dihydroxybenzoic acid cocrystal, shown in FIG. 9, displays the following peaks: $^{1}$H NMR (400 MHz, d6-DMSO) δ: 13.20 (1H), 11.66 (1H), 10.36 (1H), 8.93 (1H), 7.83 (3H), 7.56 (4H), 7.27 (2H), 6.45 (1H), 6.34 (1H), 6.27 (1H), 4.75 (1H), 3.48 (1H) and 3.24 (1H). The peak at 6.45 ppm in the $^{1}$H NMR spectrum corresponds to one CH proton of rebamipide. Comparison of the integration of this peak with that at 6.27 ppm, which corresponds to one proton on the aromatic ring of 2,4-dihydroxybenzoic acid, indicates that the cocrystal has an API:coformer stoichiometry of 1:1.

Figure 10:
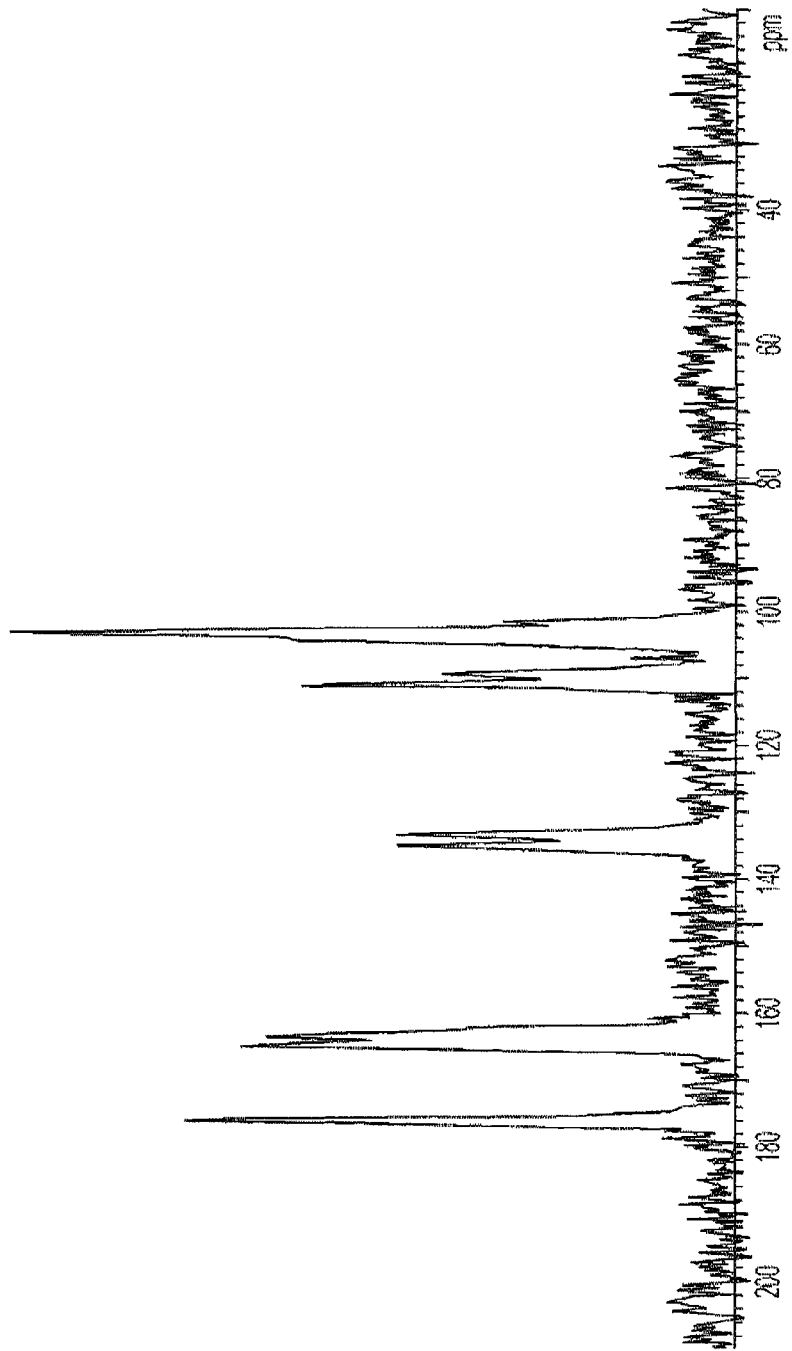
FIG. 10 shows the $^{13}$C solid state NMR spectrum of 2,4-dihydroxybenzoic acid.
Figure 11:
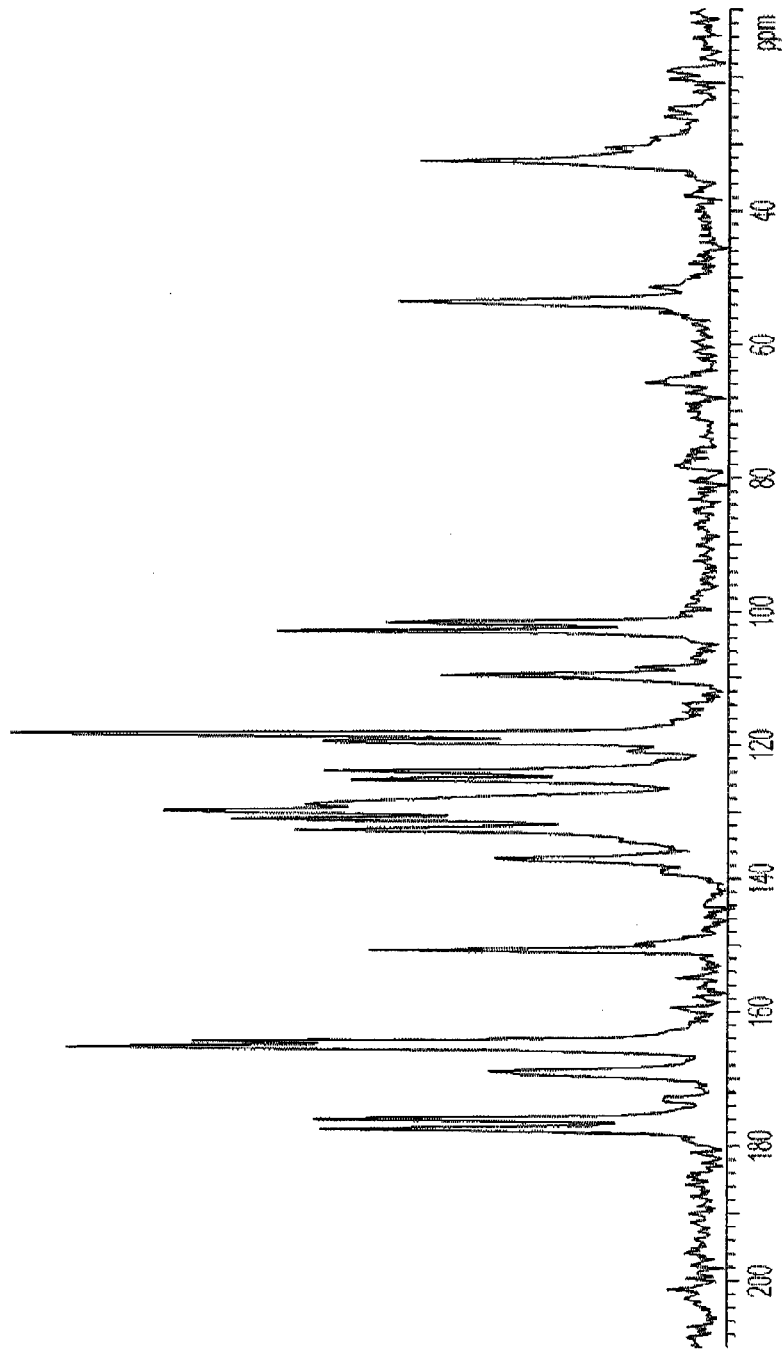
FIG. 11 shows the $^{13}$C solid state NMR spectrum of the 1:1 rebamipide 2,4-dihydroxybenzoic acid cocrystal.

2.5 $^{13}$C Solid State NMR Analysis of the 1:1 Rebamipide 2,4-dihydroxybenzoic Acid Cocrystal The $^{13}$C solid state NMR spectrum of rebamipide is shown in FIG. 4. A series of test measurements was carried out that showed that the pure rebamipide sample relaxed in such a way that a 10 s recycle delay was appropriate for this compound. When it was attempted to obtain the $^{13}$C spectra of a pure sample of 2,4-dihydroxybenzoic acid under these same acquisition conditions it was found that the 2,4-dihydroxybenzoic acid gave no signal. It was necessary to increase the recycle delay time to 90 s in order to obtain the spectrum of 2,4-dihydroxybenzoic acid (FIG. 10). The $^{13}$C spectrum obtained for the 1:1 rebamipide 2,4-dihydroxybenzoic acid cocrystal is shown in FIG. 11. Table 4 lists the characteristic shifts, ppm +/−0.5 ppm, observed in the experimental $^{13}$C NMR spectrum of FIG. 11. A recycle delay of 10 s was found to be necessary to obtain the spectrum of the cocrystal. The cocrystal does display the same relaxation behaviour as the pure API, however it can be seen that the 1:1 rebamipide 2,4-dihydroxybenzoic acid cocrystal spectrum is significantly different to those of the pure rebamipide or 2,4-dihydroxybenzoic acid. A series of test measurements showed that this recycle delay was appropriate for all the lines in the 1:1 rebamipide 2,4-dihydroxybenzoic acid cocrystal spectrum. It can, therefore, be seen the 2,4.dihydroxybenzoic acid in the 1:1 rebamipide 2,4-dihydroxybenzoic acid complex displayed much faster relaxation behaviour than when it was in its pure form. The single sample-wide relaxation behaviour of the 1:1 rebamipide 2,4-dihydroxybenzoic acid cocrystal, together with the significant changes in the $^{13}$C NMR spectrum, suggests that the two components interact and are present in the same crystal.

TABLE 4

| Chemical Shift (ppm ± 0.5 ppm) |
| --- |
| 177.7 |
| 176.1 |
| 169.1 |
| 165.4 |
| 164.6 |
| 150.9 |
| 137.1 |
| 132.9 |
| 131.3 |
| 130.1 |
| 129.2 |
| 125.4 |
| 124.1 |
| 119.7 |
| 118.5 |

TABLE 4-continued

| Chemical Shift (ppm ± 0.5 ppm) |
| --- |
| 109.7 |
| 103.1 |
| 101.8 |
| 53.7 |
| 32.6 |

The claimed invention is:

1. A 1:1 rebamipide nicotinamide cocrystal characterised by an x-ray powder diffraction pattern having at least three peaks selected from the peaks at 5.2, 9.5, 10.4, 11.5, 13.6, 16.0, 20.9 and 21.5 °2θ+0.2° 2θ.

2. A pharmaceutical composition containing a rebamipide nicotinamide cocrystal of claim 1 and a pharmaceutically acceptable carrier.

3. A method of treating or preventing a disorder selected from gastric ulcer, duodenal ulcer, gastritis, ulcerative colitis, and stomatitis, comprising the step administering to a patient in need thereof a therapeutically effective amount of a rebamipide cocrystal of claim 1.

4. A method of treating or preventing a disorder selected from gastric ulcer, duodenal ulcer, gastritis, ulcerative colitis, and stomatitis, comprising the step administering to a patient in need thereof a pharmaceutical composition comprising a therapeutically effective amount of a pharmaceutical composition of claim 2.

5. A method to accelerate salivation, to increase goblet cell density in the eye, to increase the production of mucus in the eye, to increase the production of lacrimal fluid, or to treat dry eye, comprising the step administering to a patient in need thereof a therapeutically effective amount of a rebamipide cocrystal of claim 1.

6. A method to accelerate salivation, to increase goblet cell density in the eye, to increase the production of mucus in the eye, to increase the production of lacrimal fluid, or to treat dry eye, comprising the step administering to a patient in need thereof a pharmaceutical composition comprising a therapeutically effective amount of a pharmaceutical composition of claim 2.

* * * * *